United States Patent
Taguchi et al.

(10) Patent No.: US 11,328,460 B2
(45) Date of Patent: May 10, 2022

(54) X-RAY CT SYSTEM AND PROCESSING METHOD

(71) Applicant: CANON MEDICAL SYSTEMS CORPORATION, Otawara (JP)

(72) Inventors: Hiroki Taguchi, Otawara (JP); Akshay Narayan Prabhu Verleker, Nasushiobara (JP); Yuki Houno, Otawara (JP); Satoshi Saito, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 128 days.

(21) Appl. No.: 16/716,950

(22) Filed: Dec. 17, 2019

(65) Prior Publication Data

US 2020/0193655 A1 Jun. 18, 2020

(30) Foreign Application Priority Data

Dec. 17, 2018 (JP) .............................. JP2018-235696
Dec. 17, 2018 (JP) .............................. JP2018-235697

(51) Int. Cl.
*G06T 11/00* (2006.01)
*G01N 23/046* (2018.01)
(Continued)

(52) U.S. Cl.
CPC ............ *G06T 11/005* (2013.01); *A61B 6/032* (2013.01); *A61B 6/482* (2013.01); *A61B 6/5205* (2013.01);
(Continued)

(58) Field of Classification Search
CPC ............ G06T 11/005; G06T 2211/408; G06T 11/006; G01N 23/046; G01N 2223/42;
(Continued)

(56) References Cited

U.S. PATENT DOCUMENTS 6,463,115 B1 * 10/2002 Horiuchi ................ A61B 6/032
378/4
2002/0151781 A1 * 10/2002 Ohishi ................... A61B 6/481
600/407

(Continued)

FOREIGN PATENT DOCUMENTS

JP 2015-62657 A 4/2015
JP 2016-64043 A 4/2016
(Continued)

*Primary Examiner* — David P Porta
*Assistant Examiner* — Gisselle M Gutierrez
(74) *Attorney, Agent, or Firm* — Oblon, McClelland, Maier & Neustadt, L.L.P.

(57) ABSTRACT

An X-ray CT system includes an X-ray tube, an X-ray detector and processing circuitry. The processing circuitry is configured to cyclically change energy of the X-rays during one rotation of the X-ray tube around a subject. The processing circuitry is configured to perform a process including a correcting process addressing a difference in a transmission amount between X-rays having first energy and X-rays having second energy, on at least one selected from between: a plurality of first projection data sets acquired when the X-rays having the first energy were radiated; and a plurality of second projection data sets acquired when the X-rays having the second energy were radiated. The processing circuitry is configured to reconstruct an image on the basis of a combined data set generated on the basis of a plurality of projection data sets including the projection data sets resulting from the process.

22 Claims, 7 Drawing Sheets

(51) Int. Cl.
*A61B 6/03* (2006.01)
*A61B 6/00* (2006.01)
(52) U.S. Cl.
CPC .......... *A61B 6/5235* (2013.01); *A61B 6/5258* (2013.01); *G01N 23/046* (2013.01); *G01N 2223/401* (2013.01); *G01N 2223/408* (2013.01); *G01N 2223/42* (2013.01); *G06T 2211/408* (2013.01)
(58) Field of Classification Search
CPC ....... G01N 2223/401; G01N 2223/408; G01N 2223/419; G01N 2223/423; A61B 6/032; A61B 6/482; A61B 6/5235; A61B 6/5258; A61B 6/5205
USPC .......................................................... 378/19
See application file for complete search history.

(56) References Cited

U.S. PATENT DOCUMENTS

| | | | |
|---|---|---|---|
| 2002/0156368 A1* | 10/2002 | Ohishi | A61B 6/481 600/420 |
| 2003/0109779 A1* | 6/2003 | Ohishi | A61B 6/469 600/407 |
| 2005/0074087 A1* | 4/2005 | Nukui | A61B 6/06 378/7 |
| 2006/0109951 A1* | 5/2006 | Popescu | A61B 6/032 378/4 |
| 2009/0147919 A1* | 6/2009 | Goto | A61B 6/482 378/86 |
| 2009/0161814 A1* | 6/2009 | Wu | A61B 6/505 378/5 |
| 2015/0063529 A1 | 3/2015 | Taguchi et al. | |
| 2015/0348288 A1* | 12/2015 | Hagiwara | G06T 11/006 382/131 |
| 2016/0180554 A1 | 6/2016 | Brendel | |
| 2018/0042565 A1 | 2/2018 | Wilson et al. | |
| 2018/0300879 A1* | 10/2018 | Fu | A61B 6/032 |
| 2018/0300909 A1* | 10/2018 | Tamura | A61B 6/4266 |
| 2021/0007691 A1* | 1/2021 | Prabhu Verleker | A61B 6/027 |

FOREIGN PATENT DOCUMENTS

| | | |
|---|---|---|
| JP | 2016-531692 A | 10/2016 |
| JP | 2018-511443 A | 4/2018 |

* cited by examiner

X-RAY CT SYSTEM AND PROCESSING METHOD

CROSS-REFERENCE TO RELATED APPLICATIONS

This application is based upon and claims the benefit of priority from Japanese Patent Applications No. 2018-235696 and No. 2018-235697, both filed on Dec. 17, 2018, the entire contents of all of which are incorporated herein by reference.

FIELD

Embodiments described herein relate generally to an X-ray Computed Tomography (CT) system and a processing method.

BACKGROUND

Conventionally, in X-ray Computed Tomography (CT) systems, it is possible to display a checking-purpose image used for checking movement of the subject and the imaged area or the like immediately after a scan. More specifically, the X-ray CT systems make it possible to promptly advance a subsequent workflow, by promptly providing the operator with the checking-purpose image used for checking to see whether the CT image data acquired in the scan was acquired as planned. For example, when determining that the image data was acquired as planned, by referring to the checking-purpose image displayed immediately after the scan, the operator is able to immediately allow the subject to get off the couch device. On the contrary, for example, when determining that the checking-purpose image was not acquired as planned, the operator is able to immediately re-scan the subject. In these situations, the checking-purpose image denotes, for example, an image generated without performing any image processing process such as a correction on projection data acquired in the scan.

Further, in X-ray CT systems, a technique is known by which dual-energy (DE) acquisition is performed while using X-rays having two mutually-different types of energy during a scan. Also, another technique is known by which multi-energy (ME) acquisition is performed while using X-rays having three or more mutually-different types of energy during a CT scan. By using these techniques, it is possible to acquire projection data corresponding to each type of energy and to discriminate the types, atomic numbers, density levels, and the like of substances contained in the subject by utilizing the notion that different substances have different X-ray absorption characteristics. The DE acquisition and the ME acquisition are performed, for example, by using a "rapid kV switching method (a KV switching method)" by which the energy of X-rays is changed for each of various X-ray radiation angles with respect to the subject. According to the "rapid kV switching method", for example, the energy of the X-rays is changed for every one or more views.

DETAILED DESCRIPTION

According to an embodiment, an X-ray CT system includes an X-ray tube, an X-ray detector and processing circuitry. The X-ray tube is configured to radiate X-rays while rotating around a subject. The X-ray detector is configured to detect the X-rays and to acquire a projection data set for each of rotation positions of the X-ray tube. The processing circuitry is configured to cyclically change energy of the X-rays during one rotation of the X-ray tube around the subject. The processing circuitry is configured to perform a process including a correcting process addressing a difference in a transmission amount between X-rays having first energy and X-rays having second energy, on at least one selected from between: a plurality of first projection data sets acquired when the X-rays having the first energy were radiated; and a plurality of second projection data sets acquired when the X-rays having the second energy were radiated. The processing circuitry is configured to reconstruct an image on a basis of a combined data set generated on a basis of a plurality of projection data sets including the projection data sets resulting from the process.

Exemplary embodiments of an X-ray CT system and a processing method will be explained in detail below, with reference to the accompanying drawings. Possible embodiments of the X-ray CT system and the processing method of the present disclosure are not limited to the embodiments described below.

First Embodiment

Figure 1:
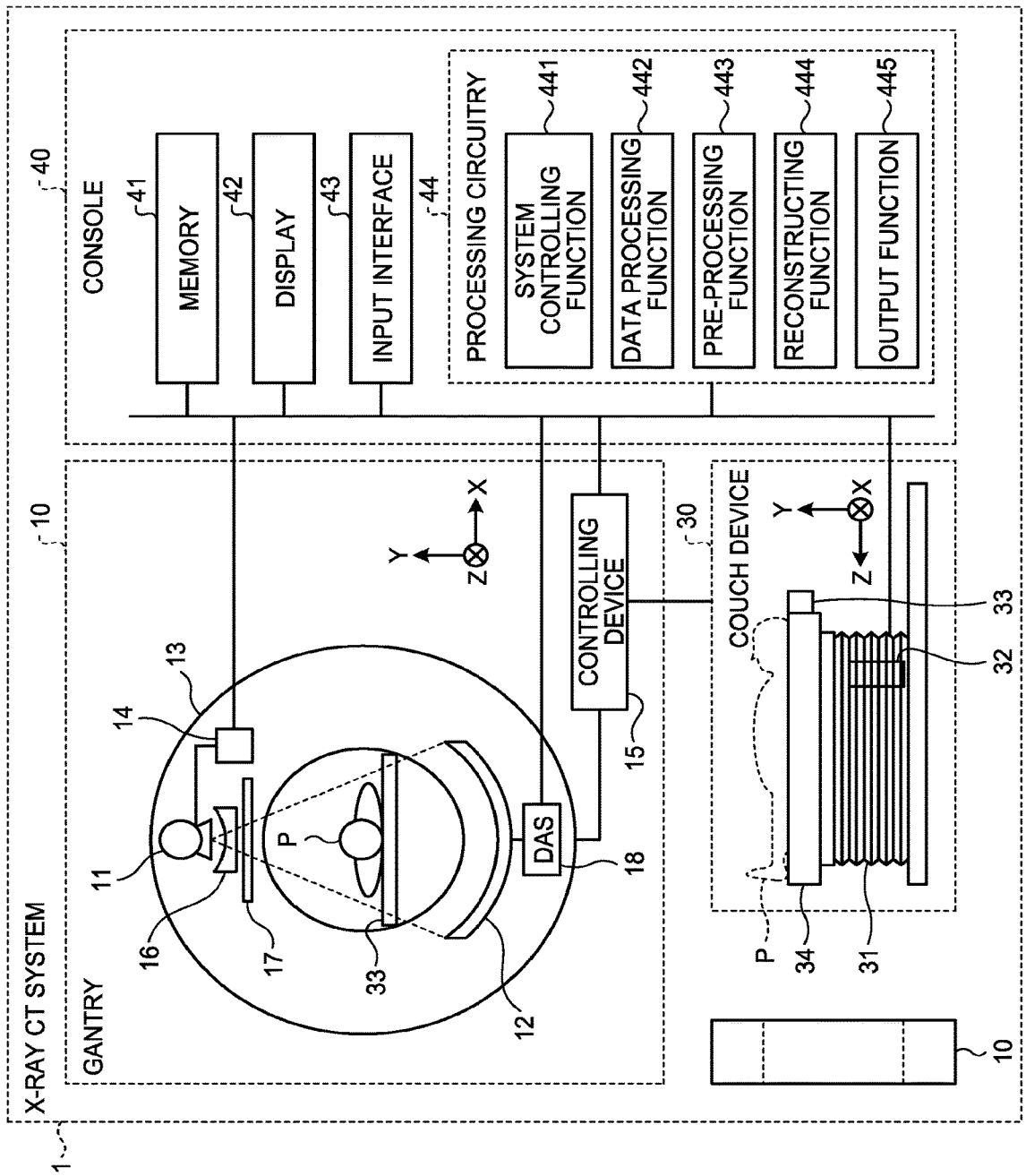
FIG. 1 is a block diagram illustrating an exemplary configuration of an X-ray CT system according to a first embodiment.

To begin with, a configuration of an X-ray CT system 1 according to a first embodiment will be explained, with reference to FIG. 1. FIG. 1 is a block diagram illustrating an exemplary configuration of the X-ray CT system 1 according to the first embodiment. As illustrated in FIG. 1, the X-ray CT system 1 includes a gantry 10, a couch device 30, and a console 40. In other words, the X-ray CT system 1 according to the first embodiment may be referred to as an X-ray CT apparatus.

In FIG. 1, the rotation axis of a rotating frame 13 in a non-tilted state or the longitudinal direction of a couchtop 33 of a couch device 30 corresponds to a Z-axis direction. Further, the axial direction orthogonal to the Z-axis direction and parallel to a floor surface corresponds to an X-axis direction. The axial direction orthogonal to the Z-axis direction and perpendicular to the floor surface corresponds to a Y-axis direction. In FIG. 1, the gantry 10 is drawn as viewed from multiple directions for the sake of convenience in the explanation. FIG. 1 illustrates the example in which the X-ray CT system 1 includes the one gantry 10.

The gantry 10 includes an X-ray tube 11, an X-ray detector 12, the rotating frame 13, an X-ray high-voltage device 14, a controlling device 15, a wedge 16, a collimator 17, and a Data Acquisition System (DAS) 18.

The X-ray tube 11 is a vacuum tube including a negative pole (a filament) configured to generate thermo electrons and a positive pole (a target) configured to generate X-rays in response to collisions of the thermo electrons. With high voltage being applied thereto from the X-ray high-voltage device 14, the X-ray tube 11 is configured to generate the X-rays to be radiated onto a subject P, by emitting the thermo electrons from the negative pole toward the positive pole. For example, the X-ray tube 11 may be an X-ray tube of a rotating anode (positive pole) type configured to generate X-rays by emitting thermo electrons onto a rotating anode. The X-ray tube 11 is an example of the X-ray tube.

The X-ray detector 12 is configured to detect X-rays that were radiated from the X-ray tube 11 and have passed through the subject P and to output a signal corresponding to a detected X-ray amount to the DAS 18. The X-ray detector 12 includes, for example, a plurality of rows of detecting elements in each of which a plurality of detecting elements are arranged in a channel direction along an arc centered on a focal point of the X-ray tube 11. For example, the X-ray detector 12 has a structure in which the plurality of rows in each of which the plurality of detecting elements are arranged in the channel direction are arranged in the row direction (a slice direction). Further, the X-ray detector 12 is, for example, a detector of an indirect conversion type including a grid, a scintillator array, and an optical sensor array. The scintillator array includes a plurality of scintillators. Each of the scintillators includes a scintillator crystal that outputs light having a photon quantity corresponding to the amount of X-rays that have become incident thereto. The grid is disposed on the surface of the scintillator array positioned on the X-ray incident side and includes an X-ray blocking plate that absorbs scattered X-rays. The grid may be referred to as a collimator (a one-dimensional collimator or a two-dimensional collimator). The optical sensor array has a function of converting outputs from the scintillators into electric signals corresponding to the amounts of light and may include, for example, optical sensors such as photodiodes. Alternatively, the X-ray detector 12 may be a detector of a direct conversion type including semiconductor elements configured to convert incident X-rays into electric signals. Further, the X-ray detector 12 is an example of the X-ray detector.

The rotating frame 13 is an annular frame configured to support the X-ray tube 11 and the X-ray detector 12 so as to oppose each other and configured to rotate the X-ray tube 11 and the X-ray detector 12 via the controlling device 15. For example, the rotating frame 13 is cast by using aluminum. In addition to supporting the X-ray tube 11 and the X-ray detector 12, the rotating frame 13 is also capable of further supporting the X-ray high-voltage device 14, the wedge 16, the collimator 17, the DAS 18, and the like. Also, the rotating frame 13 is capable of further supporting various types of structures that are not illustrated in FIG. 1. In the gantry 10, the rotating frame 13 and the part that rotates and moves together with the rotating frame 13 may hereinafter be referred to as a rotating part.

The X-ray high-voltage device 14 includes: a high-voltage generating device including electric circuits such as a transformer, a rectifier, and the like and configured to generate the high voltage to be applied to the X-ray tube 11; and an X-ray controlling device configured to control the output voltage in accordance with the X-rays to be generated by the X-ray tube 11. The high-voltage generating device may be of a transformer type or of an inverter type. Further, the X-ray high-voltage device 14 may be provided for the rotating frame 13 or for a fixed frame (not illustrated).

The controlling device 15 includes: processing circuitry having a Central Processing Unit (CPU) or the like; and a driving mechanism configured with a motor, an actuator, and the like. The controlling device 15 is configured to receive an input signal from an input interface 43 and to control operations of the gantry 10 and the couch device 30. For example, the controlling device 15 exercises control over the rotating of the rotating frame 13, the tilting of the gantry 10, operations of the couch device 30 and the couchtop 33, and the like. In one example, as the control over the tilting of the gantry 10, the controlling device 15 rotates the rotating frame 13 being centered on an axis extending parallel to the X-axis direction by using tilting angle (tilt angle) information input thereto. The controlling device 15 may be provided for the gantry 10 or for the console 40.

The wedge 16 is a filter used for adjusting the amount of X-rays radiated from the X-ray tube 11. More specifically, the wedge 16 is a filter configured to pass and attenuate the X-rays radiated from the X-ray tube 11, so that the X-rays radiated from the X-ray tube 11 onto the subject P have a predetermined distribution. For example, the wedge 16 may be a wedge filter or a bow-tie filter and is a filter obtained by processing aluminum or the like so as to have a predetermined target angle and a predetermined thickness.

The collimator 17 is structured with lead plates or the like used for narrowing down the radiation range of the X-rays that have passed through the wedge 16 and is configured to form a slit with a combination of the plurality of lead plates or the like. The collimator 17 may be referred to as an X-ray limiter. Further, although FIG. 1 illustrates the example in which the wedge 16 is arranged between the X-ray tube 11 and the collimator 17, the collimator 17 may be arranged between the X-ray tube 11 and the wedge 16. In that situation, the wedge 16 is configured to pass and attenuate the X-rays which were radiated from the X-ray tube 11 and of which the radiation range has been limited by the collimator 17.

The DAS 18 is configured to acquire the signals of the X-rays detected by the detecting elements included in the X-ray detector 12. For example, the DAS 18 includes an amplifier configured to perform an amplifying process on the electric signals output from the detecting elements; and an Analog/Digital (A/D) converter configured to convert the electric signals into digital signals. The DAS 18 is configured to generate detection data. The DAS 18 may be realized by using a processor, for example. The detection data generated by the DAS may hereinafter be referred to as projection data.

In the present example, the DAS 18 may be a DAS implementing a sequential acquisition method by which the signals of the X-rays detected by the plurality of detecting elements are sequentially acquired or may be a DAS implementing a simultaneous acquisition method by which the signals of the X-rays detected by the plurality of detecting elements are simultaneously acquired.

The data generated by the DAS 18 is transmitted, via optical communication, from a transmitter provided for the rotating frame 13 and including a Light Emitting Diode (LED) to a receiver provided in a non-rotating part (e.g., a fixed frame, which is not illustrated in FIG. 1) of the gantry 10 and including a photodiode and is further transferred to the console 40. In this situation, the non-rotating part may be, for example, the fixed frame or the like configured to rotatably support the rotating frame 13. The method for transmitting the data from the rotating frame 13 to the non-rotating part of the gantry 10 does not necessarily have to be optical communication and may be any contactless data transfer method or any contact-type data transfer method.

The couch device 30 is a device configured to have the subject P placed thereon and to move the subject P who is to be scanned. The couch device 30 includes a base 31, a couch driving device 32, the couchtop 33, and a supporting frame 34. The base 31 is a casing configured to support the supporting frame 34 so as to be movable in the vertical direction. The couch driving device 32 is a driving mechanism configured to move the couchtop 33 on which the subject P is placed, along the longitudinal direction of the couchtop 33 and includes a motor, an actuator, and the like. The couchtop 33 provided on the top face of the supporting frame 34 is a board on which the subject P is placed. In addition to moving the couchtop 33, the couch driving device 32 may also be configured to move the supporting frame 34 along the longitudinal direction of the couchtop 33.

The console 40 includes a memory 41, a display 42, an input interface 43, and processing circuitry 44. Although the console 40 is described as being separate from the gantry 10, the gantry 10 may include either the console 40 or one or more constituent elements of the console 40.

The memory 41 is realized by using, for example, a semiconductor memory element such as a Random Access Memory (RAM), a flash memory, or the like, or a hard disk, an optical disk, or the like. For example, the memory 41 is configured to store therein projection data and CT image data. Further, for example, the memory 41 is configured to store therein one or more computer programs (hereinafter, "programs") that enables the circuits included in the X-ray CT system 1 to realize the functions thereof. Alternatively, the memory 41 may be realized with a group of servers (a cloud) connected to the X-ray CT system 1 via a network.

The display 42 is configured to display various types of information. For example, the display 42 is configured to display a CT image and a checking-purpose image generated by the processing circuitry 44 and to display a Graphical User Interface (GUI) or the like used for receiving various types of operations from an operator. For example, the display 42 may be a liquid crystal display monitor or a Cathode Ray Tube (CRT) display monitor. The display 42 may be of a desktop type or may be configured with a tablet terminal or the like capable of wirelessly communicating with the main body of the console 40.

The input interface 43 is configured to receive various types of input operations from the operator, to convert the received input operations into electric signals, and to output the electric signals to the processing circuitry 44. For example, the input interface 43 receives, from the operator, an acquisition condition used when the projection data is acquired, a reconstructing condition used when CT image data is reconstructed, an image processing condition used when a CT image is generated from the CT image data, and the like. For example, the input interface 43 is realized by using a mouse, a keyboard, a trackball, a switch, a button, a joystick, a touchpad on which an input operation can be performed by touching the operation surface thereof, a touch screen in which a display screen and a touchpad are integrally formed, a contactless input circuit using an optical sensor, an audio input circuit, and/or the like. The input interface 43 may be provided for the gantry 10. Alternatively, the input interface 43 may be configured by using a tablet terminal or the like capable of wirelessly communicating with the main body of the console 40. Further, the input interface 43 does not necessarily have to include one or more physical operation component parts such as a mouse and a keyboard. For instance, possible examples of the input interface 43 include an electric signal processing circuit configured to receive an electric signal corresponding to an input operation from an external input device provided separately from the console 40 and to output the electric signal to the processing circuitry 44.

The processing circuitry 44 is configured to control operations of the entirety of the X-ray CT system 1. For example, the processing circuitry 44 is configured to execute a system controlling function 441, a data processing function 442, a pre-processing function 443, a reconstructing function 444, and an output function 445. In other words, by reading and executing programs corresponding to the functions from the memory 41, the processing circuitry 44 is configured to control the operations of the entirety of the X-ray CT system 1. The processing circuitry 44 is an example of the processing circuitry.

In the X-ray CT system 1 illustrated in FIG. 1, the processing functions are stored in the memory 41 in the form of computer-executable programs. The processing circuitry 44 is a processor configured to realize the functions corresponding to the programs, by reading and executing the programs from the memory 41. In other words, the processing circuitry 44 that has read the programs has the functions corresponding to the read programs.

Figure 2:
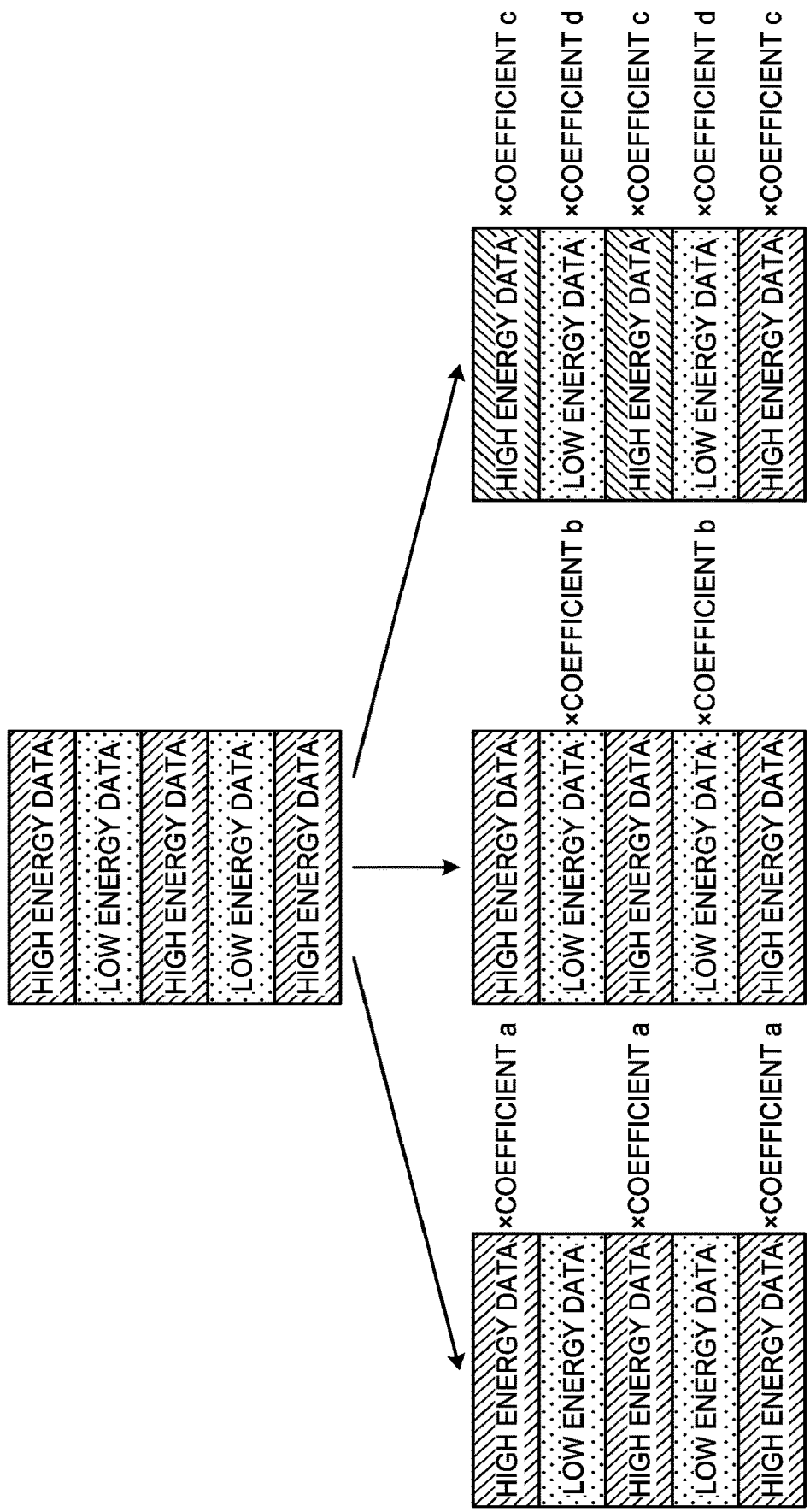
FIG. 2 is a drawing for explaining a scaling process performed by a data processing function according to the first embodiment.

Further, although FIG. 2 illustrates the example in which the processing functions, namely, the system controlling function 441, the data processing function 442, the pre-processing function 443, the reconstructing function 444, and the output function 445, are realized by the single processing circuit (i.e., the processing circuitry 44), possible embodiments are not limited to this example. For instance, the processing circuitry 44 may be structured by combining together a plurality of independent processors so that the processing functions are realized as a result of the processors executing the programs. Further, the processing functions included in the processing circuitry 44 may be realized as being distributed among, or integrated together into, one or more processing circuits, as appropriate.

The system controlling function 441 is configured to control various types of processes performed by the X-ray CT system 1 on the basis of input operations received from the operator via the input interface 43. For example, by controlling the couch driving device 32, the collimator 17, the controlling device 15, the X-ray high-voltage device 14, and the like included in the X-ray CT system 1, the system controlling function 441 is configured to perform a position determining scan and a main scan.

In the present example, the system controlling function 441 controls an "imaging process implementing a dual energy scheme" by using the "rapid kV switching method". More specifically, by transmitting a control signal that switches between high voltage and low voltage to the X-ray high-voltage device 14, the system controlling function 441 controls application of high voltage and low voltage from the X-ray high-voltage device 14 to the X-ray tube 11. Further, by transmitting a control signal to the DAS 18, the system controlling function 441 exercises control so that the DAS 18 identifies whether the detection data detected thereby is derived from high-voltage X-ray radiation or derived from low-voltage X-ray radiation.

The data processing function 442 is configured to generate the projection data used for generating a checking-purpose image, by performing various types of processes on projection data acquired by performing the "imaging process implementing a dual energy scheme" by using the "rapid kV switching method". More specifically, the data processing function 442 is configured to generate the projection data used for generating the checking-purpose image, by performing a scaling process or the like on the detection data (the projection data) generated by the DAS 18. For example, the data processing function 442 generates the projection data used for generating the checking-purpose image, by performing a process on at least one selected from between: projection data corresponding to first X-ray tube voltage (e.g., high voltage) and projection data corresponding to second X-ray tube voltage (e.g., low voltage). The projection data generated by the data processing function 442 is stored into the memory 41. Details of the processes performed by the data processing function 442 will be explained later. Further, in the following sections, pieces of projection data that are acquired by alternately switching the X-ray tube voltage levels while using the "rapid kV switching method" and that correspond to the mutually-different X-ray tube voltage levels will be referred to as projection data sets.

The pre-processing function 443 is configured to generate post-pre-processing projection data by performing correcting processes such as a logarithmic converting process, an offset correction, a sensitivity correction, a beam hardening correction, and/or the like on the detection data (the projection data) transmitted thereto from the DAS 18. For example, the pre-processing function 443 generates a post-pre-processing projection data set from the detection data (the projection data) corresponding to the first X-ray tube voltage (e.g., the high voltage). Further, the pre-processing function 443 generates a post-pre-processing projection data set from the detection data (the projection data) corresponding to the second X-ray tube voltage (e.g., the low voltage).

Further, by using two types of projection data sets, the pre-processing function 443 is configured to separate predetermined two or more reference substances (water, iodine, calcium, hydroxyapatite, fat, and/or the like) that are present in a site subject to an imaging process. Further, the pre-processing function 443 generates two or more types of post-pre-processing projection data sets using monochromatic X-rays that correspond to the two or more reference substances, respectively. For example, from the post-pre-processing projection data set corresponding to the high energy and the post-pre-processing projection data set corresponding to the low energy, the pre-processing function 443 generates post-pre-processing projection data sets using monochromatic X-rays each corresponding to water and iodine, respectively. The post-pre-processing projection data sets generated by the pre-processing function 443 are stored into the memory 41.

The reconstructing function 444 is configured to generate various types of images from the post-pre-processing projection data sets stored in the memory 41 and to store the generated images into the memory 41. For example, the reconstructing function 444 is configured to obtain reconstructed CT image data by reconstructing the post-pre-processing projection data while using any of various reconstructing methods (e.g., back projection methods such as a Filtered Back Projection (FBP) method and successive approximation methods) and to further store the reconstructed CT image data into the memory 41. Further, by performing any of various image processing processes, the reconstructing function 444 is configured to generate a CT image such as a MultiPlanar Reconstruction (MPR) image from the CT image data and to store the generated CT image into the memory 41.

For example, the reconstructing function 444 reads the post-pre-processing projection data sets of the reference substances using the monochromatic X-rays that are stored in the memory 41 and reconstructs reference substance image data (reference substance highlighted image data). In one example, the reconstructing function 444 reconstructs reference substance image data of a water component on the basis of the post-pre-processing projection data set in which the water component is emphasized and reconstructs reference substance image data of an iodine component on the basis of the post-pre-processing projection data set in which the iodine component is emphasized. Further, the reconstructing function 444 generates a reference substance image of the water component and a reference substance image of the iodine component, by performing an image processing process on the reference substance image data of the water component and the reference substance image data of the iodine component. Further, by performing a weighted calculation process while using the two pieces of reference substance image data, the reconstructing function 444 is able to generate various types of images such as a monochromatic X-ray image corresponding to a predetermined energy level, a density image, and an effective atomic number image.

Further, for example, the reconstructing function 444 is configured to read the post-pre-processing projection data set corresponding to the high energy and the post-pre-processing projection data set corresponding to the low energy each stored in the memory 41 and to further reconstruct CT image data from each of the post-pre-processing projection data sets. After that, the reconstructing function 444 is also capable of generating a multicolor X-ray image corresponding to the high energy and a multicolor X-ray image corresponding to the low energy from the CT image data.

Further, the reconstructing function 444 is configured to obtain reconstructed CT image data by reconstructing the projection data sets generated by the data processing function 442 while using any of various reconstructing methods (e.g., back projection methods such as the Filtered Back Projection (FBP) method and successive approximation methods) and to further store the reconstructed CT image data into the memory 41. Further, the reconstructing function 444 is configured to generate a checking-purpose image from the CT image data by performing any of various image processing processes and to store the generated checking-purpose image into the memory 41.

The output function 445 is configured to cause the display 42 to display the CT image and the checking-purpose image generated by the reconstructing function 444 and the like.

An overall configuration of the X-ray CT system 1 according to the present embodiment has thus been explained. The X-ray CT system 1 according to the present embodiment structured as described above makes it possible to efficiently acquire the checking-purpose image used for checking an imaged range or the like. More specifically, the X-ray CT system 1 makes it possible to promptly provide the checking-purpose image while keeping a certain level of image quality, even when image taking processes are performed by using a plurality of mutually-different levels of energy while using the "rapid kV switching method".

As explained above, in the image taking processes using the "rapid kV switching method", because the energy of the X-rays is changed for every one or more views, pieces of projection data corresponding to mutually-different energy levels are present in a mixed manner. For this reason, the X-ray transmission amounts are different among the pieces of projection data corresponding to the different energy levels. For example, the X-ray transmission amount corresponding to the high energy is larger than that corresponding to the low energy. Accordingly, when a checking-purpose image is generated by using such projection data sets, an artifact may occur, and there may be some situations where the image is not usable for the checking purpose. Further, for example, although it is possible to generate a checking-purpose image by using only projection data set corresponding to one energy level, because the data would be thinned out, a part of the data would be missing. As a result, an artifact might occur, and the image might be unusable for the checking purpose in some situations.

To cope with these situations, the X-ray CT system 1 according to the present embodiment is configured to generate a checking-purpose image in which artifacts are reduced, by performing a correcting process addressing the difference in the transmission amount between mutually-different energy levels. More specifically, in the X-ray CT system 1, the difference in the transmission amount is reduced by processes performed by the data processing function 442. In the following sections, the process to reduce the difference in the transmission amount will be referred to as a scaling process.

The data processing function 442 is configured to perform a process including a correcting process addressing the difference in the transmission amount between X-rays having first energy and X-rays having second energy, on at least one selected from between: a plurality of first projection data sets acquired when the X-rays having the first energy were radiated; and a plurality of second projection data sets acquired when the X-rays having the second energy were radiated. More specifically, the data processing function 442 performs the correcting process on at least one selected from between the plurality of first projection data sets and the plurality of second projection data sets so as to reduce the difference in the transmission amount between the X-rays having the first energy and the X-rays having the second energy.

FIG. 2 is a drawing for explaining the scaling process performed by the data processing function 442 according to the first embodiment. FIG. 2 illustrates a part of the projection data acquired by performing the "imaging process implementing the dual energy scheme" by using the "rapid kV switching method". In other words, the rectangles of high energy and the rectangles of low energy in FIG. 2 represent the projection data sets output from the DAS 18 as a result of the X-ray detector 12 acquiring the X-rays radiated while switching between the high energy and the low energy for every one or more views.

For example, the data processing function 442 performs a correcting process of multiplying one selected from between the plurality of first projection data sets and the plurality of second projection data sets, by a coefficient based on the difference in the transmission amount. In one example, as illustrated in the bottom left section of FIG. 2, the data processing function 442 multiplies each of the high energy projection data sets ("HIGH ENERGY DATA" in FIG. 2) by a "coefficient a". In other words, the data processing function 442 multiplies each of the values of the pieces of projection data corresponding to the views and being included in the high energy projection data sets, by the "coefficient a". In this situation, the "coefficient a" is a coefficient calculated on the basis of the difference in the transmission amount and used for approximating the X-ray transmission amount of the high energy projection data sets to the X-ray transmission amount of the low energy projection data sets.

Alternatively, for example, as illustrated in the bottom middle section of FIG. 2, the data processing function 442 multiplies each of the low energy projection data sets ("LOW ENERGY DATA" in FIG. 2) by a "coefficient b". In other words, the data processing function 442 multiplies each of the values of the pieces of projection data corresponding to the views and being included in the low energy projection data sets, by the "coefficient b". In this situation, the "coefficient b" is a coefficient calculated on the basis of the difference in the transmission amount and used for approximating the X-ray transmission amount of the low energy projection data sets to the X-ray transmission amount of the high energy projection data sets.

In this situation, the "coefficient a" and the "coefficient b" are calculated in advance and stored in the memory 41. For example, the high energy data and the low energy data are acquired in advance, and the difference in the X-ray transmission amount is calculated. After that, the coefficients are calculated from the calculated difference in the transmission amount and stored in the memory 41. Such coefficients are stored in the memory 41 in correspondence with various sets each made up of different energy levels. The data processing function 442 performs the scaling process by reading, from the memory 41, a coefficient corresponding to a set of energy levels currently being used.

As another process using the multiplication by a coefficient, for example, the data processing function 442 may perform a correcting process by multiplying the plurality of first projection data sets by a coefficient based on the difference between the first energy and third energy and multiplying the plurality of second projection data sets by a coefficient based on the difference between the second energy and the third energy. In other words, the data processing function 442 multiplies the projection data sets corresponding to each of the different energy levels by the coefficients, so as to approximate the X-ray transmission amounts to an X-ray transmission amount corresponding to one targeted energy level. In this situation, the third energy is energy between the first energy and the second energy, for example.

In one example, as illustrated in the bottom right section of FIG. 2, the data processing function 442 multiplies each of the pieces of high energy data by a "coefficient c" and multiplies each of the pieces of low energy data by a "coefficient d". In other words, the data processing function 442 multiplies each of the values of the pieces of projection data corresponding to the views and being included in the high energy projection data sets by the "coefficient c" and multiplies each of the values of the pieces of projection data corresponding to the views and being included in the low energy projection data sets by the "coefficient d". In this situation, the "coefficient c" is a coefficient used for approximating the X-ray transmission amount of the high energy projection data sets to an X-ray transmission amount of the targeted energy level. Further, the "coefficient d" is a coefficient used for approximating the X-ray transmission amount of the low energy projection data sets to the X-ray transmission amount of the targeted energy level.

In this situation, it is possible to perform the abovementioned scaling process using the "coefficient c" and the "coefficient d", through adaptive use of a process in a beam hardening correction. For example, in the beam hardening correction, a correcting process is performed on acquired projection data so as to approximate the transmission amount to the transmission amount of targeted monochromatic energy. Accordingly, the data processing function 442 performs the correcting process on the high energy projection data sets and the low energy projection data sets so as to approximate the transmission amounts to the transmission amount of the targeted monochromatic energy. As a result, the transmission amount of the high energy projection data sets and the transmission amount of the low energy projection data sets become approximate to the transmission amount of the targeted monochromatic energy. As a result, the transmission amounts of the two become approximate to each other.

In the embodiments described above, the example is explained in which, when the one or more coefficients used in the scaling process are calculated from the actual difference in the transmission amount, the coefficients used in the beam hardening correction are applied as the coefficients used in the scaling process; however, possible embodiments are not limited to this example. It is also acceptable to use values that are theoretically calculated. For example, it is also acceptable to logically calculate the X-ray transmission amount corresponding to the first energy and the X-ray transmission amount corresponding to the second energy and to further calculate one or more coefficients from the difference between the calculated transmission amounts.

As explained above, the data processing function 442 is configured to perform the correcting process of multiplying the one selected from between the plurality of first projection data sets and the plurality of second projection data sets by the one or more coefficients based on the difference in the transmission amount. As a result, the X-ray CT system 1 is able to reduce the difference in the X-ray transmission amount within the projection data sets in which the mutually-different levels of energy are present in a mixed manner and is thus able to generate a checking-purpose image in which artifacts are reduced.

For example, the reconstructing function 444 is able to generate a checking-purpose image in which artifacts are reduced, by using the data in any of the three projection data sets resulting from the multiplication with the coefficients illustrated at the bottom of FIG. 2.

In this situation, the X-ray CT system 1 according to the first embodiment is further capable of performing a process to reduce artifacts. More specifically, the data processing function 442 is configured to perform an interpolation process to generate a plurality of first interpolation data sets corresponding to rotation positions from which the first energy was not radiated on the basis of the plurality of first projection data sets and to generate a plurality of second interpolation data sets corresponding to rotation positions from which the second energy was not radiated on the basis of the plurality of second projection data sets. Further, the data processing function 442 is configured: to generate first combined data sets by combining together the first projection data sets and the second interpolation data sets of which the rotation positions of the X-ray radiation unit correspond to each other; and to generate second combined data sets by combining together the second projection data sets and the first interpolation data sets of which the rotation positions correspond to each other.

Figure 3:
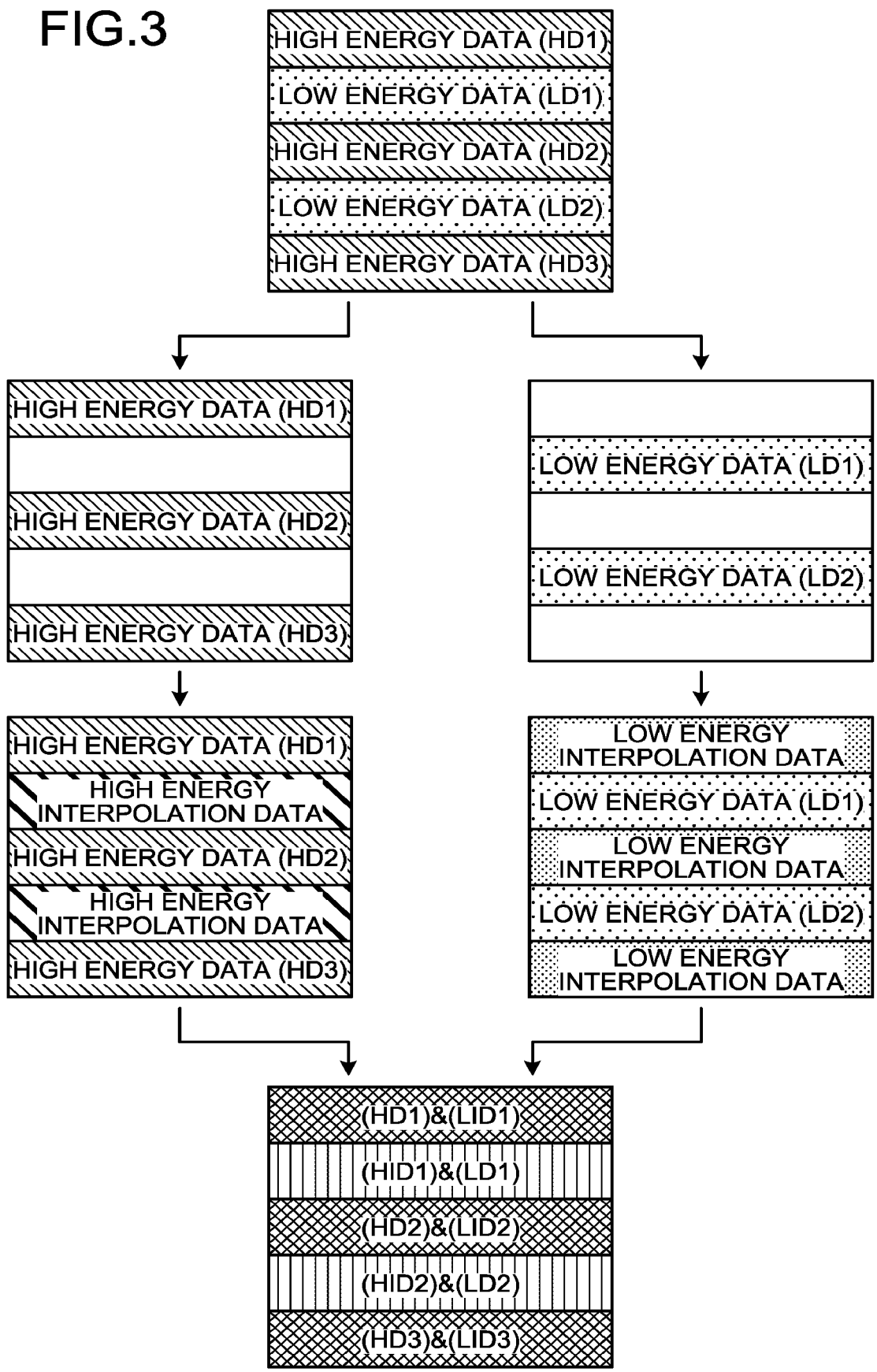
FIG. 3 is a drawing for explaining a process performed by a data processing function according to the first embodiment.

FIG. 3 is a drawing for explaining a process performed by the data processing function 442 according to the first embodiment. FIG. 3 illustrates a process performed after the scaling process illustrated in FIG. 2. In other words, the projection data sets illustrated at the top section of FIG. 3 correspond to any one of the blocks of projection data sets multiplied with the coefficients illustrated in the bottom section of FIG. 2.

For example, as illustrated in FIG. 3, the data processing function 442 separates the projection data sets in which the pieces of high energy data and the pieces of low energy data are present in a mixed manner, into projection data sets of high energy data and projection data sets of low energy data. After that, as illustrated in FIG. 3, the data processing function 442 generates the data in missing parts by performing an interpolation process, with respect to the projection data sets of the high energy data and the projection data sets of the low energy data.

For example, by using the plurality of projection data sets corresponding to the high energy, the data processing function 442 generates interpolation data sets for the missing parts (the rotation positions from which the X-rays having the high energy are not radiated). Similarly, by using the plurality of projection data sets corresponding to the low energy, the data processing function 442 generates interpolation data sets for the missing parts (the rotation positions from which the X-rays having the low energy are not radiated). In other words, the data processing function 442 generates the high energy interpolation data sets for the rotation positions from which the X-rays having the low energy were radiated and generates the low energy interpolation data sets for the rotation positions from which the X-rays having the high energy were radiated.

As for the method of the interpolation process performed by the data processing function 442, it is possible to use any interpolation method such as a linear interpolation method, a Lagrangian interpolation method, a sigmoid method, or the like, as long as it is possible to generate the interpolation data sets from the projection data sets.

Further, with respect to each of the rotation positions, the data processing function 442 generates a combined data set by combining the actually-acquired projection data set with the generated interpolation data set. For example, as illustrated in FIG. 3, the data processing function 442 generates a combined data set "(HD1) & (LID1)" by combining high energy data (HD1) with low energy interpolation data (LID1). Further, as illustrated in FIG. 3, the data processing function 442 generates a combined data set "(HID1) & (LD1)" by combining high energy interpolation data (HID1) with low energy data (LD1). Similarly, the data processing function 442 generates combined data sets by combining the actually-acquired projection data sets with the generated interpolation data sets.

In this situation, to use information from the actually-acquired projection data in a larger amount, the data processing function 442 performs the combining process by applying a heavier weight to the actually-acquired projection data sets than to the interpolation data sets. For example, by using a formula "$(W_b \times HD1)+(1-W_b) \times LID1$" using a weight "$W_b$", the data processing function 442 arranges the weight to satisfy "$W_b=0.75$", when generating the combined data set "(HD1) & (LID1)". With this arrangement, the information amount from the high energy data (HD1) is larger in the combined data set "(HD1) & (LID1)". Similarly, when generating the other combined data sets, the data processing function 442 performs the combining process by applying a heavier weight to the actually-acquired projection data sets than to the interpolation data sets.

The reconstructing function 444 is configured to generate the checking-purpose image by performing a reconstructing process or the like on the projection data sets (the plurality of combined data sets) resulting from the combining process performed by the data processing function 442. The output function 445 is configured to cause the display 42 to display the checking-purpose image generated by the reconstructing function 444. In this situation, the checking-purpose image denotes an image displayed shortly after the scan (immediately after the scan) and used for checking the range that was imaged (the imaged range). In other words, immediately after the checking-purpose image is generated by the reconstructing function 444, the output function 445 causes the display 42 to display the checking-purpose image.

As explained above, the X-ray CT system 1 according to the first embodiment is able to generate the checking-purpose image in which artifacts are further reduced, by reducing artifacts with the scaling process and further performing the combining process on the projection data sets resulting from the scaling process.

Figure 4:
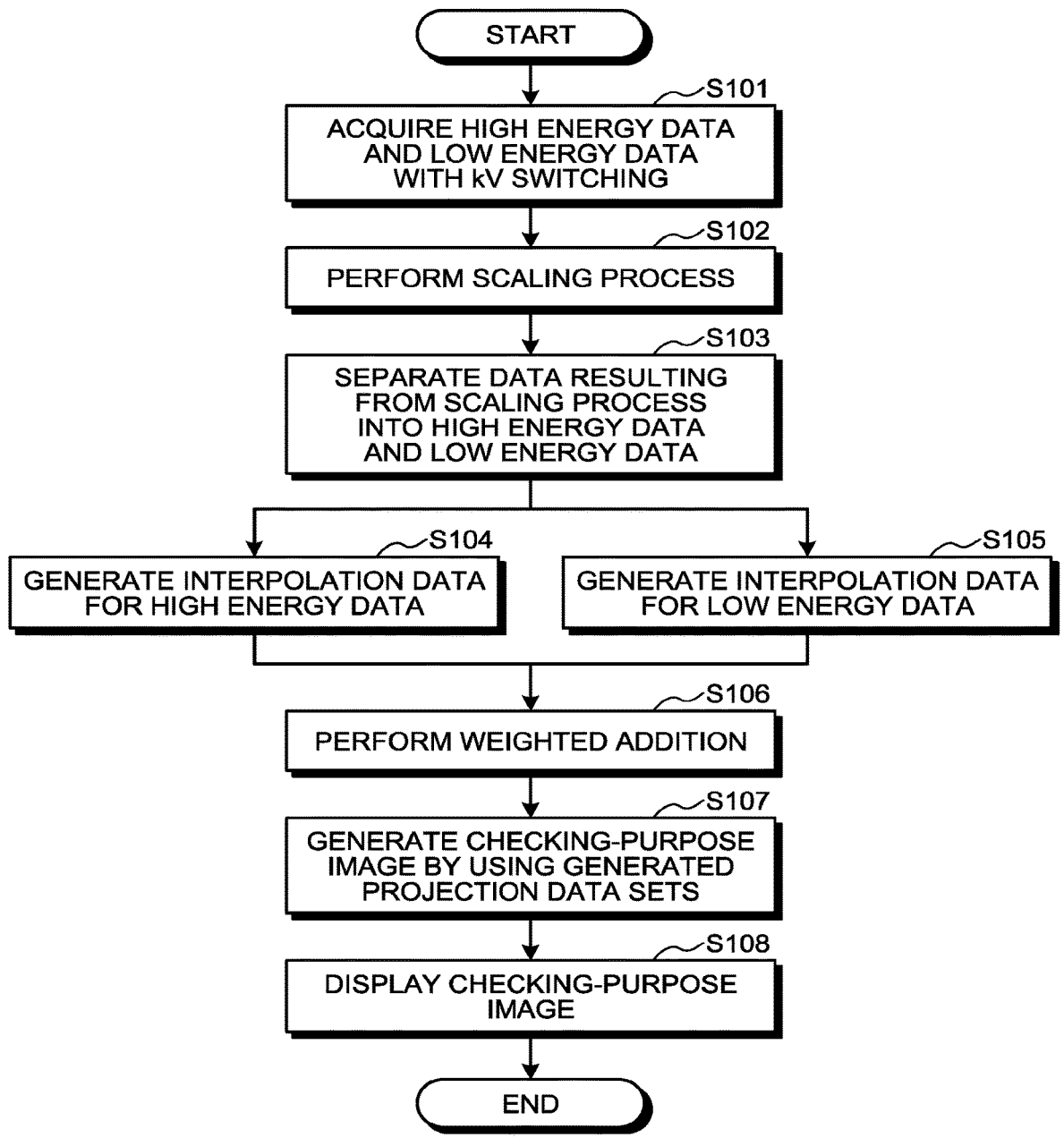
FIG. 4 is a flowchart for explaining a flow in processes performed by the X-ray CT system according to the first embodiment.

Next, an example of a procedure of the processes performed by the X-ray CT system 1 will be explained, with reference to FIG. 4. FIG. 4 is a flowchart for explaining a flow in the processes performed by the X-ray CT system 1 according to the first embodiment. In the present example, FIG. 4 illustrates an example in which the combining process is performed after the scaling process. Further, FIG. 4 illustrates the example in which a checking-purpose image is displayed in the "imaging process implementing the dual energy scheme".

Step S101 is a step realized as a result of the processing circuitry 44 reading and executing a program corresponding to the system controlling function 441. Steps S102 through S106 are steps realized as a result of the processing circuitry 44 reading and executing a program corresponding to the data processing function 442. Step S107 is a step realized as a result of the processing circuitry 44 reading and executing a program corresponding to the reconstructing function 444. Step S108 is a step realized as a result of the processing circuitry 44 reading and executing a program corresponding to the output function 445.

At first, the processing circuitry 44 acquires high energy data and low energy data by using the "rapid kV switching method" (step S101). Subsequently, the processing circuitry 44 performs the scaling process (step S102) and separates the data resulting from the scaling process into high energy data and low energy data (step S103). After that, the processing circuitry 44 generates interpolation data for the high energy data and interpolation data for the low energy data (steps S104 and S105).

Further, the processing circuitry 44 performs weighted addition so that information from the actually-acquired projection data sets is contained in a larger amount (step S106). After that, the processing circuitry 44 generates a checking-purpose image by using the generated projection data sets (step S107) and causes the display 42 to display the checking-purpose image (step S108).

As explained above, according to the first embodiment, the X-ray tube 11 is configured to radiate the X-rays while rotating around the subject. The system controlling function 441 is configured to cyclically change the energy of the X-rays during one rotation of the X-ray tube 11 around the subject. The X-ray detector 12 is configured to detect the X-rays and to acquire a projection data set for each of the rotation positions of the X-ray radiation unit. The data processing function 442 is configured to perform the process including the correcting process addressing the difference in the transmission amount between the X-rays having the first energy and the X-rays having the second energy, on at least one selected from between: the plurality of first projection data sets acquired when the X-rays having the first energy were radiated and the plurality of second projection data sets acquired when the X-rays having the second energy were radiated. The reconstructing function 444 is configured to reconstruct the image on the basis of the combined data sets generated on the basis of the plurality of projection data sets including the projection data sets resulting from the process. Consequently, the X-ray CT system 1 according to the first embodiment is able to reduce artifacts based on the difference in the X-ray transmission amount between the projection data sets acquired by using the "rapid kV switching method" and thus makes it possible to efficiently acquire the checking-purpose image used for the purpose of checking the imaged range, or the like.

The present embodiment is applicable to both systems in which the X-ray tube voltage is switched for every view and systems in which the X-ray tube voltage is switched for every two or more views. In both of the situations, it is possible to generate a checking-purpose image in which artifacts are reduced. In particular, in the systems in which the X-ray tube voltage is switched for every two or more views, because the rotation angle of the acquisition using the same energy is large, a significant amount of artifacts would occur in the checking-purpose image. Consequently, it is more effective to apply the present embodiment to such systems in which the X-ray tube voltage is switched for every two or more views.

Further, according to the first embodiment, the data processing function 442 is configured to perform the correcting process on at least one selected from between the plurality of first projection data sets and the plurality of second projection data sets so as to reduce the difference in the transmission amount between the X-rays having the first energy and the X-rays having the second energy. Consequently, the X-ray CT system 1 according to the first embodiment makes it possible to reduce the difference in the X-ray transmission amount between the projection data sets acquired by using the "rapid kV switching method".

Further, according to the first embodiment, the data processing function 442 is configured to perform the correcting process by multiplying one selected from between the plurality of first projection data sets and the plurality of second projection data sets by the coefficient based on the difference in the transmission amount. Consequently, the X-ray CT system 1 according to the first embodiment makes it possible to easily reduce the difference in the X-ray transmission amount between the projection data sets acquired by using the "rapid kV switching method".

Further, according to the first embodiment, the data processing function 442 is configured to perform the correcting process by multiplying the plurality of first projection data sets by the coefficient based on the difference between the first energy and the third energy and multiplying the plurality of second projection data sets by the coefficient based on the difference between the second energy and the third energy. Consequently, the X-ray CT system 1 according to the first embodiment makes it possible to cause the X-ray transmission amounts of the projection data sets acquired by using the "rapid kV switching method" to be equal to the transmission amount corresponding to the desired level of energy.

Further, according to the first embodiment, the process performed by the data processing function 442 includes the interpolation process to generate the plurality of first interpolation data sets corresponding to the rotation positions from which the first energy was not radiated on the basis of the plurality of first projection data sets and to generate the plurality of second interpolation data sets corresponding to the rotation positions from which the second energy was not radiated on the basis of the plurality of second projection data sets. The data processing function 442 is configured to generate the first combined data sets by combining together the first projection data sets and the second interpolation data sets of which the rotation positions of the X-ray tube 11 correspond to each other and to generate the second combined data sets by combining together the second projection data sets and the first interpolation data sets of which the rotation positions correspond to each other. The reconstructing function 444 is configured to reconstruct the image by using the first combined data sets and the second combined data sets. Consequently, the X-ray CT system 1 according to the first embodiment makes it possible to further reduce artifacts.

Further, according to the first embodiment, the data processing function 442 is configured to generate the first combined data sets and the second combined data sets by applying the weights so that the proportions of the first projection data sets and the second projection data sets are higher therein, respectively. Consequently, the X-ray CT system 1 according to the first embodiment makes it possible to generate the checking-purpose image containing the information from the acquired data in a larger amount.

Other Embodiments

The first embodiment has thus been explained. It is, however, also possible to carry out the present disclosure in various different modes other than those described in the first embodiment.

Figure 5:
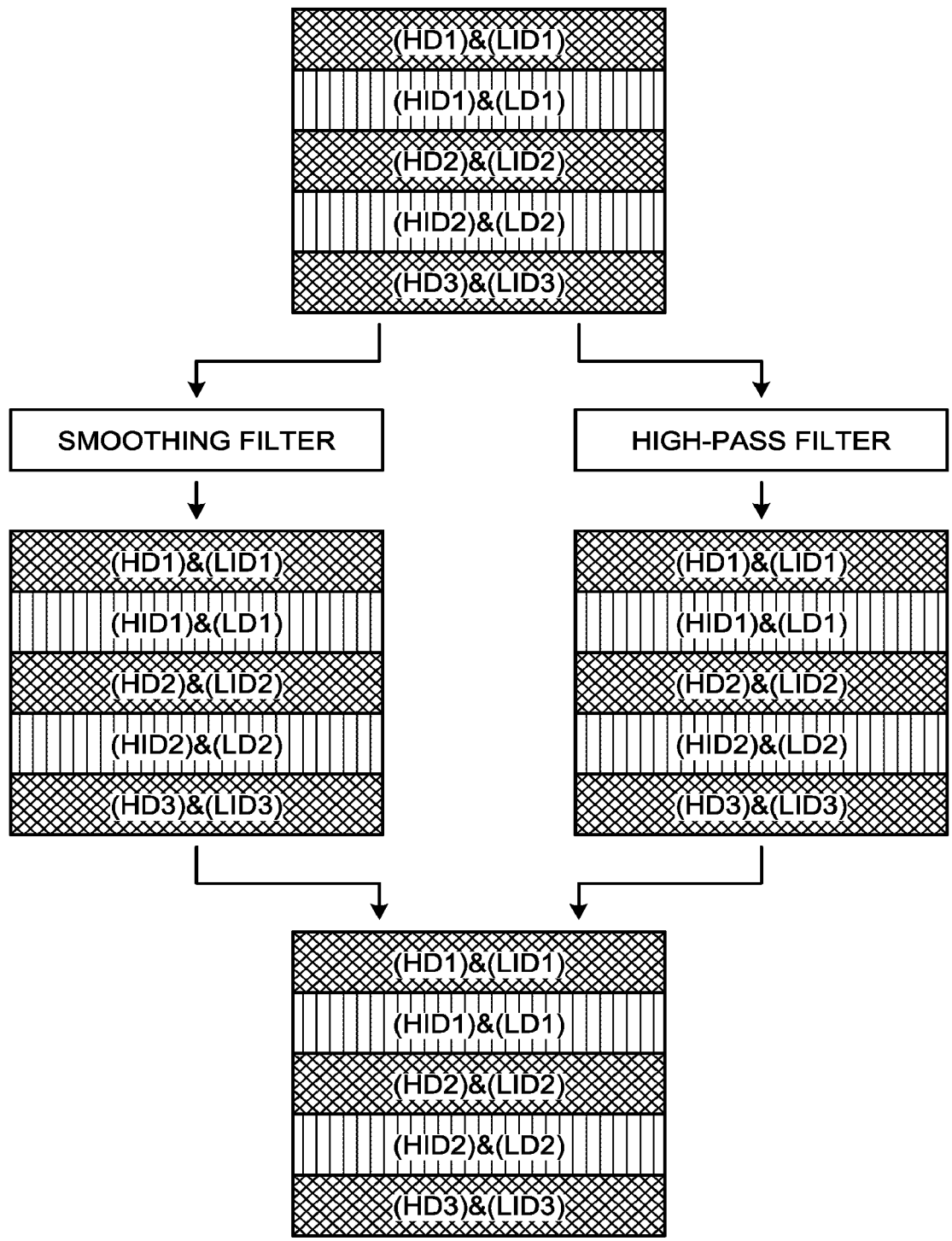
FIG. 5 is a drawing for explaining a filtering process performed by a data processing function according to another embodiment.

In the first embodiment above, the example was explained in which the checking-purpose image is generated from the projection data sets resulting from the combining process; however, possible embodiments are not limited to this example. It is also possible to further perform a filtering process on the projection data sets resulting from the combining process. FIG. 5 is a drawing for explaining the filtering process performed by the data processing function 442 according to another embodiment. FIG. 5 illustrates the projection data sets resulting from the combining process (the plurality of combined data sets) illustrated in FIG. 3.

For example, after applying mutually-different filters to the plurality of projection data sets, the data processing function 442 combines together the plurality of projection data sets resulting from the application. In one example, as illustrated in FIG. 5, the data processing function 442 makes duplicates of the projection data sets resulting from the combining process and applies a smoothing filter and a high-pass filter to the duplicated projection data sets, respectively. Further, the data processing function 442 generates filtered projection data sets by combining together the projection data sets to which the filters were applied.

In one example, the data processing function 442 generates a combined data set "(HD1) & (LID1)" by combining a combined data set "(HD1) & (LID1)" to which the smoothing filter has been applied, with a combined data set "(HD1) & (LID1)" to which the high-pass filter has been applied. Similarly, with respect to the other combined data sets corresponding to the other rotation positions also, the data processing function 442 generates combined data sets by combining the combined data sets to which the smoothing filter has been applied, with the combined data sets to which the high-pass filter has been applied.

In the combining process described above, the data processing function 442 may generate the combined data sets so as to contain, in an equal amount to each other, the information from the combined data sets to which the smoothing filter has been applied and the information from the combined data sets to which the high-pass filter has been applied. Alternatively, the data processing function 442 may also perform a weighting process similar to that in the combining process described in the first embodiment. In other words, the data processing function 442 may perform the combining process so that information from one selected from between the following is contained in a larger amount: the combined data sets to which the smoothing filter has been applied; and the combined data sets to which the high-pass filter has been applied.

When the information from the combined data sets to which the smoothing filter has been applied and the information from the combined data sets to which the high-pass filter has been applied are contained in an equal amount to each other, for example, the data processing function 442 combines together the combined data sets to which the smoothing filter has been applied and the combined data sets to which the high-pass filter has been applied, after applying a weight "0.5" to each. In contrast, when performing the combining process so that the information from one of the two is contained in a larger amount, the data processing function 442 combines the combined data sets to which the smoothing filter has been applied and the combined data sets to which the high-pass filter has been applied, after applying a weight having a larger value to one of the two.

With this arrangement, it is possible to reduce partial streak artifacts that may remain in the combined data sets prior to the filtering process. In the description above, the example was explained in which the filtering process is performed by using both the smoothing filter and the high-pass filter; however, it is also acceptable to use one of the filters for the filtering process.

In the first embodiment above, the example of the "imaging process implementing the dual energy scheme" was explained; however, possible embodiments are not limited to this example. The present disclosure is also applicable to projection data sets acquired by an "imaging process implementing a multi energy scheme" that uses X-rays having three or more mutually-different types of energy.

Further, in the first embodiment above, the example was explained in which the interpolation data sets for the missing parts (the rotation positions from which the X-rays having the high energy were not radiated) are generated by using the plurality of projection data sets having the high energy, whereas the interpolation data sets for the missing parts (the rotation positions from which the X-rays having the low energy were not radiated) are generated by using the plurality of projection data sets having the low energy; however, possible embodiments are not limited to this example. Another arrangement is also acceptable in which interpolation data sets are generated with respect to only such rotation positions that correspond to transition time periods occurring at the time of switching between the energy levels.

For example, when the high energy is "140 kVp", whereas the low energy is "80 kVp", a transition time period occurs when the X-ray tube voltage is switched. In other words, in the time period when the energy changes from "140 kVp" to "80 kVp", there is a transition time period during which the X-ray tube voltage gradually falls. Conversely, in the time period when the energy changes from "80 kVp" to "140 kVp", there is a transition time period during which the X-ray tube voltage gradually rises. During these transition time periods, projection data sets are acquired as a result of X-rays being radiated while the X-ray tube voltage is changing.

Accordingly, the data processing function 442 may generate interpolation data sets for only the missing parts in the rotation positions corresponding to the transition time periods. In other words, for the projection data sets resulting from the scaling process, the data processing function 442 generates the interpolation data sets from the actually-acquired projection data sets with respect to the rotation positions corresponding to the transition time periods.

Further, in the first embodiment, the example was explained in which the interpolation data is generated after performing the scaling process; however, possible embodiments are not limited to this example. The X-ray CT system 1 may generate the interpolation data without performing the scaling process. In other words, the X-ray CT system 1 according to the present embodiment may generate a checking-purpose image in which artifacts are reduced, by generating the interpolation data sets used for the interpolation of the missing parts present in the projection data sets acquired by using the mutually-different energy levels and further performing the combining process to combine the generated interpolation data sets with the actually-acquired projection data sets.

In that situation, the data processing function 442 performs a process including an interpolation process to generate a plurality of first interpolation data sets corresponding to the rotation positions from which the first energy was not radiated on the basis of the plurality of first projection data sets acquired when the X-rays having the first energy were radiated and to generate a plurality of second interpolation data sets corresponding to the rotation positions from which the second energy was not radiated on the basis of the plurality of second projection data sets acquired when the X-rays having the second energy were radiated. After that, the data processing function 442 generates first combined data sets by combining together the first projection data sets and the second interpolation data sets of which the rotations positions of the X-ray tube 11 correspond to each other and also generates second combined data sets by combining together the second projection data sets and the first interpolation data sets of which the rotations positions correspond to each other.

Next, an example of generating the interpolation data without performing the scaling process will be explained, with reference to FIG. 3. In that situation, FIG. 3 illustrates, for example, a part of the projection data acquired by performing the "imaging process implementing the dual energy scheme" by using the "rapid kV switching method". In other words, the rectangles of the high energy and the rectangles of the low energy in FIG. 3 represent the projection data sets output from the DAS 18 as a result of the X-ray detector 12 acquiring the X-rays radiated while switching between the high energy and the low energy for every one or more views.

For example, as illustrated in FIG. 3, the data processing function 442 separates the projection data sets in which the pieces of high energy data and the pieces of low energy data are present in a mixed manner, into projection data sets of high energy data and projection data sets of low energy data. After that, as illustrated in FIG. 3, the data processing function 442 generates the data in the missing parts by performing the interpolation process, with respect to the projection data sets of the high energy data and the projection data sets of the low energy data.

For example, by using the plurality of projection data sets corresponding to the high energy, the data processing function 442 generates the interpolation data sets for the missing parts (the rotation positions from which the X-rays having the high energy are not radiated). Similarly, by using the plurality of projection data sets corresponding to the low energy, the data processing function 442 generates the interpolation data sets for the missing parts (the rotation positions from which the X-rays having the low energy are not radiated). In other words, the data processing function 442 generates the high energy interpolation data sets for the rotation positions from which the X-rays having the low energy were radiated and generates the low energy interpolation data sets for the rotation positions from which the X-rays having the high energy were radiated.

As for the method of the interpolation process performed by the data processing function 442, it is possible to use any interpolation method such as a linear interpolation method, a Lagrangian interpolation method, a sigmoid method, or the like, as long as it is possible to generate the interpolation data sets from the projection data sets.

Further, with respect to each of the rotation positions, the data processing function 442 generates a combined data set by combining the actually-acquired projection data set with the generated interpolation data set. For example, as illustrated in FIG. 3, the data processing function 442 generates a combined data set "(HD1) & (LID1)" by combining high energy data (HD1) with low energy interpolation data (LID1). Further, as illustrated in FIG. 3, the data processing function 442 generates a combined data set "(HID1) & (LD1)" by combining high energy interpolation data (HID1) with low energy data (LD1). Similarly, the data processing function 442 generates combined data sets by combining the actually-acquired projection data sets with the generated interpolation data sets.

In this situation, to use information from the actually-acquired projection data in a larger amount, the data processing function 442 performs the combining process by applying a heavier weight to the actually-acquired projection data sets than to the interpolation data sets. For example, by using the formula "$(W_b \times HD1)+(1-W_b) \times LID1$" using the weight "$W_b$", the data processing function 442 arranges the weight to satisfy "$W_b=0.75$", when generating the combined data set "(HD1) & (LID1)". With this arrangement, the information amount from the high energy data (HD1) is larger in the combined data set "(HD1) & (LID1)". Similarly, when generating the other combined data sets, the data processing function 442 performs the combining process by applying a heavier weight to the actually-acquired projection data sets than to the interpolation data sets.

The reconstructing function 444 is configured to generate the checking-purpose image by performing a reconstructing process or the like on the projection data sets (the plurality of combined data sets) resulting from the combining process performed by the data processing function 442. The output function 445 is configured to cause the display 42 to display the checking-purpose image generated by the reconstructing function 444.

As explained above, the X-ray CT system 1 according to said another embodiment is able to generate the checking-purpose image in which artifacts are reduced, by generating the interpolation data sets for the missing parts and further performing the combining process on the acquired projection data sets.

In the embodiments above, the example was explained in which the interpolation data sets are generated and are subsequently combined with the actually-acquired projection data sets; however, possible embodiments are not limited to this example. Another arrangement is also acceptable in which a checking-purpose image is generated by using projection data sets in which the interpolation was performed on the missing parts. In one example, a checking-purpose image may be generated by using the projection data sets resulting from the interpolation process that are illustrated in the third section from the top in FIG. 3. In that situation, the reconstructing function 444 generates the checking-purpose image by using one selected from between: the high energy projection data sets interpolated with the interpolation data; and the low energy projection data sets interpolated with the interpolation data.

In this situation, the X-ray CT system 1 according to said another embodiment is able to perform a process to further reduce artifacts. More specifically, the data processing function 442 further reduces artifacts by further performing a filtering process on the projection data sets resulting from the combining process.

In the following sections, the example of performing the filtering process will be explained, with reference to FIG. 5. In the present example, FIG. 5 illustrates the projection data sets resulting from the combining process (the plurality of combined data sets) illustrated in FIG. 3.

For example, after applying the mutually-different filters to the plurality of projection data sets, the data processing function 442 combines together the plurality of projection data sets resulting from the application. In one example, as illustrated in FIG. 5, the data processing function 442 makes duplicates of the projection data sets resulting from the combining process and applies the smoothing filter and the high-pass filter to the duplicated projection data sets, respectively. Further, the data processing function 442 generates filtered projection data sets by combining together the projection data sets to which the filters were applied.

In one example, the data processing function 442 generates a combined data set "(HD1) & (LID1)" by combining the combined data set "(HD1) & (LID1)" to which the smoothing filter has been applied, with the combined data set "(HD1) & (LID1)" to which the high-pass filter has been applied. Similarly, with respect to the other combined data sets corresponding to the other rotation positions also, the data processing function 442 generates combined data sets by combining the combined data sets to which the smoothing filter has been applied, with the combined data sets to which the high-pass filter has been applied.

In the combining process described above, the data processing function 442 may generate the combined data sets so as to contain, in an equal amount to each other, the information from the combined data sets to which the smoothing filter has been applied and the information from the combined data sets to which the high-pass filter has been applied. Alternatively, the data processing function 442 may also apply a weight to one of the two types of information. In other words, the data processing function 442 may perform the combining process so that information from one selected from between the following is contained in a larger amount: the combined data sets to which the smoothing filter has been applied; and the combined data sets to which the high-pass filter has been applied.

When the information from the combined data sets to which the smoothing filter has been applied and the information from the combined data sets to which the high-pass filter has been applied are contained in an equal amount to each other, for example, the data processing function 442 combines together the combined data sets to which the smoothing filter has been applied and the combined data sets to which the high-pass filter has been applied, after applying a weight "0.5" to each. In contrast, when performing the combining process so that the information from one of the two is contained in a larger amount, the data processing function 442 combines the combined data sets to which the smoothing filter has been applied and the combined data sets to which the high-pass filter has been applied, after applying a weight having a larger value to one of the two.

With this arrangement, it is possible to reduce partial streak artifacts that may remain in the combined data sets prior to the filtering process. In the description above, the example was explained in which the filtering process is performed by using both the smoothing filter and the high-pass filter; however, it is also acceptable to use one of the filters for the filtering process.

Figure 6:
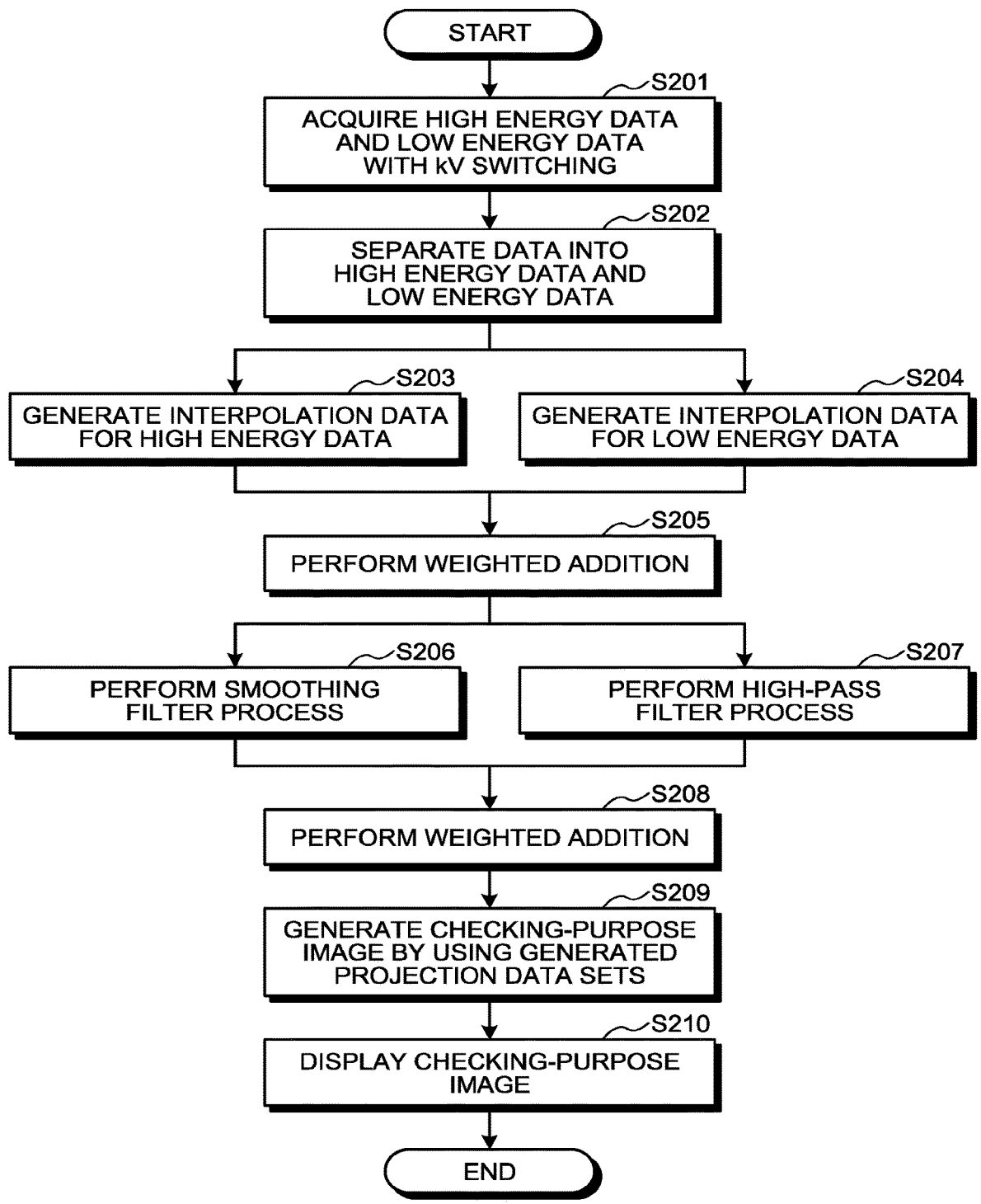
FIG. 6 is a flowchart for explaining a flow in processes performed by an X-ray CT system according to said another embodiment.

Next, an example of a procedure of the processes performed by the X-ray CT system 1 when generating interpolation data without performing the scaling process will be explained, with reference to FIG. 6. FIG. 6 is a flowchart for explaining a flow in the processes performed by the X-ray CT system 1 according to said another embodiment. In the present example, FIG. 6 illustrates an example in which the filtering process is performed after the combining process. Further, FIG. 6 illustrates the example in which a checking-purpose image is displayed in the "imaging process implementing the dual energy scheme".

Step S201 is a step realized as a result of the processing circuitry 44 reading and executing a program corresponding to the system controlling function 441. Steps S202 through S208 are steps realized as a result of the processing circuitry 44 reading and executing a program corresponding to the data processing function 442. Step S209 is a step realized as a result of the processing circuitry 44 reading and executing a program corresponding to the reconstructing function 444. Step S210 is a step realized as a result of the processing circuitry 44 reading and executing a program corresponding to the output function 445.

At first, the processing circuitry 44 acquires high energy data and low energy data by using the "rapid kV switching method" (step S201). Subsequently, the processing circuitry 44 separates the data into high energy data and low energy data (step S202). After that, the processing circuitry 44 generates interpolation data for the high energy data and interpolation data for the low energy data (steps S203 and S204).

Subsequently, the processing circuitry 44 performs weighted addition so that information from the actually-acquired projection data sets is contained in a larger amount (step S205) and performs a smoothing filter process and a high-pass filter process on the projection data sets resulting from the addition (steps S206 and S207). Further, the processing circuitry 44 performs weighted addition so that desired information is contained in a larger amount (step S208). After that, the processing circuitry 44 generates a checking-purpose image by using the generated projection data sets (step S209) and causes the display 42 to display the checking-purpose image (step S210).

As explained above, according to said another embodiment, the X-ray tube 11 is configured to radiate the X-rays while rotating around the subject. The system controlling function 441 is configured to cyclically change the energy of the X-rays, during one rotation of the X-ray tube 11 around the subject. The X-ray detector 12 is configured to detect the X-rays and to acquire a projection data set for each of the rotation positions of the X-ray radiation unit. The data processing function 442 is configured to perform the process including the interpolation process to generate the plurality of first interpolation data sets corresponding to the rotation positions from which the first energy was not radiated on the basis of the plurality of first projection data sets acquired when the X-rays having the first energy were radiated and to generate the plurality of second interpolation data sets corresponding to the rotation positions from which the second energy was not radiated on the basis of the plurality of second projection data sets acquired when the X-rays having the second energy were radiated. The reconstructing function 444 is configured to reconstruct the image on the basis of the combined data sets generated on the basis of the plurality of projection data sets including the projection data sets resulting from the process. Consequently, the X-ray CT system 1 according to said another embodiment is able to generate the checking-purpose image in which artifacts are reduced, by generating the projection data sets with the interpolation for the missing parts in the projection data sets acquired by using the "rapid kV switching method" and thus makes it possible to efficiently acquire the checking-purpose image used for the purpose of checking the imaged range, or the like.

The present embodiments are applicable to both systems in which the X-ray tube voltage is switched for every view and systems in which the X-ray tube voltage is switched for every two or more views. In both of the situations, it is possible to generate a checking-purpose image in which artifacts are reduced. In particular, in the systems in which the X-ray tube voltage is switched for every two or more views, because the rotation angle of the acquisition using the same energy is large, a significant amount of artifacts would occur in the checking-purpose image. Consequently, it is more effective to apply the present embodiments to such systems in which the X-ray tube voltage is switched for every two or more views.

Further, according to said another embodiment, the combined data sets are generated by applying the mutually-different filters to the plurality of projection data sets, respectively, and subsequently combining together the plurality of projection data sets resulting from the application. Consequently, the X-ray CT system 1 according to said another embodiment makes it possible to further reduce artifacts.

Further, according to said another embodiment, the data processing function 442 is configured to generate the first combined data sets by combining together the first projection data sets and the second interpolation data sets of which the rotation positions of the X-ray tube 11 correspond to each other and to generate the second combined data sets by combining together the second projection data sets and the first interpolation data sets of which the rotation positions correspond to each other. The reconstructing function 444 is configured to reconstruct the image by using the first combined data sets and the second combined data sets. Consequently, the X-ray CT system 1 according to said another embodiment is able to more accurately perform the interpolation for the missing parts and thus makes it possible to further reduce artifacts.

Further, according to said another embodiment, the data processing function 442 is configured to generate the first combined data sets and the second combined data sets by applying the weights so that the proportions of the first projection data sets and the second projection data sets are higher therein, respectively. Consequently, the X-ray CT system 1 according to said another embodiment makes it possible to generate the checking-purpose image containing the information from the acquired data in a larger amount.

Further, the X-ray CT system 1 according to the first embodiment was described as the system (the X-ray CT apparatus) in which the gantry 10, the couch device 30, and the console 40 are connected to one another; however, possible embodiments are not limited to this example. For instance, an X-ray CT system of the present disclosure may be structured so that a part of the processes described above is performed by apparatuses provided on a network in a distributed manner.

Figure 7:
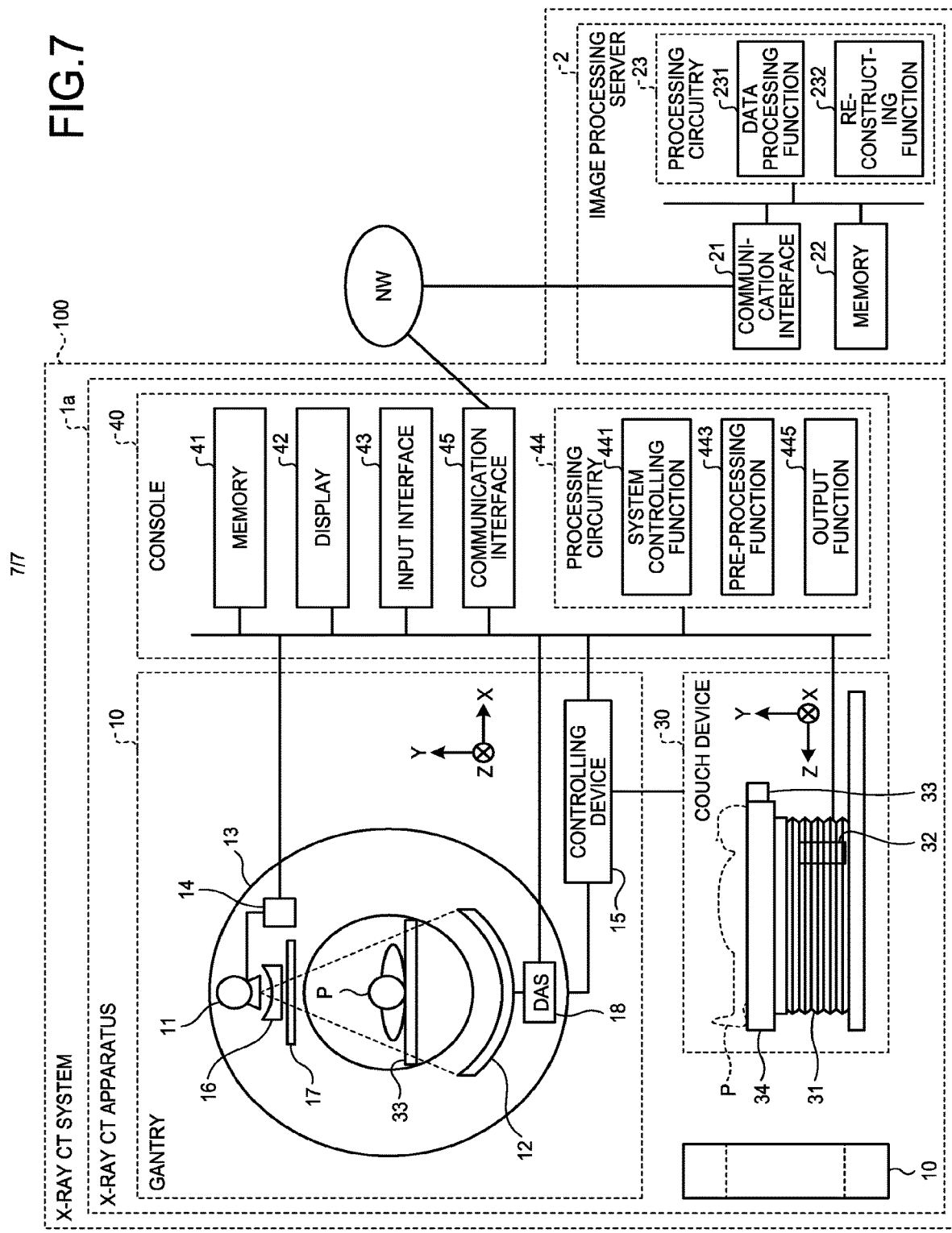
FIG. 7 is a block diagram illustrating an exemplary configuration of an X-ray CT system according to yet another embodiment.

FIG. 7 is a block diagram illustrating an exemplary configuration of an X-ray CT system 100 according to yet another embodiment. The X-ray CT system 100 according to said yet another embodiment is different from the X-ray CT system 1 illustrated in FIG. 1 for including an image processing server 2 and in that the X-ray CT apparatus 1*a* includes a communication interface 45 and is connected to the image processing server 2 via a network NW. In the following sections, some of the constituent elements that are the same as those explained in the first embodiment will be referred to by using the same reference characters as those used in FIG. 1, and the explanations thereof will be omitted.

The communication interface 45 is connected to the processing circuitry 44 and is configured to control transmission of various types of data to/from, and communication with, the image processing server 2 connected via the network NW. For example, the communication interface 45 is realized by using a network card, network adaptor, a Network Interface Controller (NIC), or the like. In one example, the communication interface 45 is configured to transmit the projection data sets generated by the DAS 18 to the image processing server 2. Further, the communication interface 45 is configured to receive the projection data sets resulting from the process from the image processing server 2 and to output the received projection data sets to the processing circuitry 44.

The image processing server 2 includes a communication interface 21, a memory 22, and processing circuitry 23.

The communication interface 21 is connected to the processing circuitry 23 and is configured to control transmission of various types of data to/from, and communication with, the X-ray CT apparatus connected via the network NW. For example, the communication interface 21 is realized by using a network card, a network adaptor, a Network Interface Controller (NIC), or the like. In one example, the communication interface 21 is configured to receive the projection data sets from the X-ray CT apparatus and to output the received projection data sets to the processing circuitry 23. Further, the communication interface 21 is configured to output the projection data sets resulting from the process performed by the processing circuitry 23, to the X-ray CT apparatus.

The memory 22 is connected to the processing circuitry 23 and is connected to store various types of data therein. For example, the memory 22 is realized by using a semiconductor memory element such as a Random Access Memory (RAM), a flash memory, or the like, or a hard disk, an optical disk, or the like. For example, the memory is configured to store therein the projection data sets received from the X-ray CT apparatus. Further, the memory 22 is configured to store therein the programs corresponding to processing functions executed by the processing circuitry 23.

The processing circuitry 23 executes a data processing function 231 and a reconstructing function 232. In other words, the processing circuitry 23 is configured to control operations of the image processing server by reading and executing the programs corresponding to the functions from the memory 22. More specifically, the data processing function 231 is configured to perform the same processes as those performed by the data processing function 442 described above. Further, the reconstructing function 232 is configured to perform the same processes as those performed by the reconstructing function 444 described above. The processing circuitry 23 is an example of the processing circuitry.

In the image processing server 2 illustrated in FIG. 7, the processing functions are stored in the memory 22 in the form of computer-executable programs. The processing circuitry 23 is a processor configured to realize the functions corresponding to the programs, by reading and executing the programs from the memory 22. In other words, the processing circuitry 23 that has read the programs has the functions corresponding to the read programs.

Further, although FIG. 7 illustrates the example in which the processing functions, namely, the data processing function 231 and the reconstructing function 232, are realized by the single processing circuit (i.e., the processing circuitry 23), possible embodiments are not limited to this example. For instance, the processing circuitry 23 may be structured by combining together a plurality of independent processors so that the processing functions are realized as a result of the processors executing the programs. Further, the processing functions included in the processing circuitry 23 may be realized as being distributed among, or integrated together into, one or more processing circuits, as appropriate.

The term "processor" used in the above explanations denotes, for example, a CPU, a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the memory 41 or the memory 22.

FIG. 1 illustrates the example in which the single memory (the memory 41) stores therein the programs corresponding to the processing functions. FIG. 7 illustrates the example in which the single memory (the memory 22) stores therein the programs corresponding to the processing functions. However, possible embodiments are not limited to these examples. For instance, it is acceptable to provide a plurality of memories 41 in a distributed manner, so that the processing circuitry 44 reads a corresponding program from each of the individual memories 41. Further, for example, it is also acceptable to provide a plurality of memories 22 in a distributed manner, so that the processing circuitry 23 reads a corresponding program from each of the individual memories 22. Further, instead of saving the programs in either the memory 41 or the memory 22, it is also acceptable to directly incorporate the programs into the circuits of one or more processors. In that situation, the one or more processors realize the functions by reading and executing the programs incorporated in the circuit thereof.

The constituent elements of the apparatuses and the devices described in the embodiments above are based on functional concepts. Thus, it is not necessary to physically configure the constituent elements as indicated in the drawings. In other words, specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a program analyzed and executed by the CPU or may be realized as hardware using wired logic.

It is possible to realize the processing program described in any of the embodiments above by causing a computer such as a personal computer or a workstation to execute the processing program prepared in advance. It is possible to distribute the processing program via a network such as the Internet. Further, it is also possible to record the processing program onto a computer-readable recording medium such as a hard disk, a flexible disk (FD), a Compact Disk Read-Only Memory (CD-ROM), a Magneto Optical (MO) disk, a Digital Versatile Disk (DVD), or the like, so as to be executed as being read from the recording medium by a computer.

According to at least one aspect of the embodiments described above, it is possible to efficiently obtain the checking-purpose image used for the purpose of checking the imaged range, or the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT system, comprising:
an X-ray tube configured to radiate X-rays while rotating around a subject;
an X-ray detector configured to detect the X-rays and to acquire a projection data set for each of rotation positions of the X-ray tube; and
processing circuitry configured to
cyclically change energy of the X-rays during one rotation of the X-ray tube around the subject,
perform a process, including a correcting process addressing a difference in a transmission amount between X-rays having a first energy and X-rays having a second energy, on at least one selected from among a plurality of first projection data sets acquired when the X-rays having the first energy were radiated and a plurality of second projection data sets acquired when the X-rays having the second energy were radiated, and
reconstruct an image based on a combined data set generated based on a plurality of projection data sets including the projection data sets resulting from the process.

2. The X-ray CT system according to claim 1, wherein the processing circuitry is further configured to perform the correcting process on at least one selected from among the plurality of first projection data sets and the plurality of second projection data sets, so as to reduce the difference in the transmission amount between the X-rays having the first energy and the X-rays having the second energy.

3. The X-ray CT system according to claim 2, wherein the processing circuitry is further configured to perform the correcting process by multiplying one selected from between the plurality of first projection data sets and the plurality of second projection data sets by a coefficient based on the difference in the transmission amount.

4. The X-ray CT system according to claim 2, wherein the processing circuitry is further configured to perform the correcting process by multiplying the plurality of first projection data sets by a coefficient based on a difference between the first energy and a third energy and multiplying the plurality of second projection data sets by a coefficient based on a difference between the second energy and the third energy.

5. The X-ray CT system according to claim 1, wherein the process performed by the processing circuitry includes an interpolation process of generating a plurality of first interpolation data sets corresponding to a rotation position from which the X-rays having the first energy were not radiated based on the plurality of first projection data sets, and generating a plurality of second interpolation data sets corresponding to a rotation position from which the X-rays having the second energy were not radiated based on the plurality of second projection data sets.

6. The X-ray CT system according to claim 5, wherein the processing circuitry is further configured to
generate a first combined data set by combining together the first projection data sets and the second interpolation data sets of which rotation positions of the X-ray tube correspond to each other,
generate a second combined data set by combining together the second projection data sets and the first interpolation data sets of which rotation positions correspond to each other, and
reconstruct an image by using the first combined data set and the second combined data set.

7. The X-ray CT system according to claim 6, wherein the processing circuitry is further configured to generate the first combined data set and the second combined data set by applying weights so that proportions of the first projection data set and the second projection data set are higher therein, respectively.

8. The X-ray CT system according to claim 1, wherein the image reconstructed by the processing circuitry is an image for checking an imaged range.

9. The X-ray CT system according to claim 1, wherein the processing circuitry is further configured to display the image immediately after a scan.

10. The X-ray CT system according to claim 1, wherein the processing circuitry is further configured to generate a plurality of first interpolation data sets corresponding to projection data sets of the first energy and a plurality of second interpolation data sets corresponding to projection data sets of the second energy with respect to rotation positions corresponding to transition time periods occurring at a time of switching between the first energy and the second energy during one rotation of the X-ray tube.

11. The X-ray CT system according to claim 2, wherein the processing circuitry is further configured to perform the correcting process by multiplying one selected from among the plurality of first projection data sets and the plurality of second projection data sets by a coefficient used for approximating, of the first energy and the second energy in the X-rays emitted during one rotation of the X-ray tube, an X-ray transmission amount of one energy to an X-ray transmission amount of an other energy.

12. A processing method that uses a projection data set acquired for each of rotation positions while an energy of X-rays is cyclically changed during one rotation around an subject, the processing method comprising:
performing a process, including a correcting process addressing a difference in a transmission amount between X-rays having a first energy and X-rays having a second energy, on at least one selected from among a plurality of first projection data sets acquired when the X-rays having the first energy were radiated and a plurality of second projection data sets acquired when the X-rays having the second energy were radiated; and
reconstructing an image based on a combined data set generated based on a plurality of projection data sets including the projection data sets resulting from the process.

13. The processing method according to claim 12, wherein the correcting process is performed on at least one selected from among the plurality of first projection data sets and the plurality of second projection data sets, so as to reduce the difference in the transmission amount between the X-rays having the first energy and the X-rays having the second energy.

14. The processing method according to claim 13, wherein the correcting process is performed by multiplying one selected from among the plurality of first projection data sets and the plurality of second projection data sets by a coefficient based on the difference in the transmission amount.

15. The processing method according to claim 13, wherein the correcting process is performed by multiplying the plurality of first projection data sets by a coefficient based on a difference between the first energy and a third energy and multiplying the plurality of second projection data sets by a coefficient based on a difference between the second energy and the third energy.

16. The processing method according to claim 12, wherein the process includes an interpolation process of generating a plurality of first interpolation data sets corresponding to a rotation position from which the X-rays having the first energy were not radiated based on the plurality of first projection data sets, and generating a plurality of second interpolation data sets corresponding to a rotation position from which the X-rays having the second energy were not radiated based on the plurality of second projection data sets.

17. The processing method according to claim 16, further comprising
generating a first combined data set by combining together the first projection data sets and the second interpolation data sets of which rotation positions correspond to each other,
generating a second combined data set by combining together the second projection data sets and the first interpolation data sets of which rotation positions correspond to each other, and
reconstructing an image by using the first combined data set and the second combined data set.

18. The processing method according to claim 17, wherein the steps of generating the first combined data set and generating the second combined data set further comprise applying weights so that proportions of the first projection data set and the second projection data set are higher therein, respectively.

19. The processing method according to claim 12, further comprising checking an imaged range using the image.

20. The processing method according to claim 12, further comprising displaying the image immediately after a scan.

21. The processing method according to claim 12, wherein the correcting process is performed by generating a plurality of first interpolation data sets corresponding to projection data sets of the first energy and a plurality of second interpolation data sets corresponding to projection data sets of the second energy with respect to rotation positions corresponding to transition time periods occurring at a time of switching between the first energy and the second energy during one rotation of the X-ray tube.

22. The processing method according to claim 13, wherein the correcting process is performed by multiplying one selected from among the plurality of first projection data sets and the plurality of second projection data sets by a coefficient used for approximating, of the first energy and the second energy in the X-rays emitted during one rotation of the X-ray tube, an X-ray transmission amount of one energy to an X-ray transmission amount of an other energy.

* * * * *